United States Patent
Clark et al.

(10) Patent No.: US 11,033,697 B2
(45) Date of Patent: Jun. 15, 2021

(54) NASAL DRUG DELIVERY DEVICES

(71) Applicant: Eli Lilly and Company, Indianapolis, IN (US)

(72) Inventors: Sarah Louise Clark, Somerville, MA (US); Naser Ibrahim Hineiti, Carmel, IN (US); Matthew Glenn Kawiecki, Indianapolis, IN (US); Mehul Sanmukh Patel, Zionsville, IN (US); Andrew Thomas Snow, Fishers, IN (US); Matthew Scott Thomas, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/958,056

(22) PCT Filed: Jan. 17, 2020

(86) PCT No.: PCT/US2020/013985
§ 371 (c)(1),
(2) Date: Jun. 25, 2020

(87) PCT Pub. No.: WO2020/154182
PCT Pub. Date: Jul. 30, 2020

(65) Prior Publication Data
US 2020/0398006 A1 Dec. 24, 2020

Related U.S. Application Data

(60) Provisional application No. 62/796,155, filed on Jan. 24, 2019.

(51) Int. Cl.
*A61M 15/08* (2006.01)
*A61M 15/00* (2006.01)
*A61M 11/02* (2006.01)

(52) U.S. Cl.
CPC ............ *A61M 15/08* (2013.01); *A61M 11/02* (2013.01); *A61M 15/0036* (2014.02);
(Continued)

(58) Field of Classification Search
CPC . A61D 7/04; A61J 1/2013; A61J 1/201; A61J 1/2003; A61M 5/3015; A61M 5/155;
(Continued)

(56) References Cited

U.S. PATENT DOCUMENTS 3,853,125 A  12/1974  Clark et al.
4,861,335 A * 8/1989  Reynolds ............ A61M 5/2448
                                                     604/88
(Continued)

FOREIGN PATENT DOCUMENTS

GB    2367756        4/2002
GB    2367756 A  *  4/2002  ........ A61M 15/0041
(Continued)

OTHER PUBLICATIONS

Patent Cooperation Treaty International Search Report of the International Searching Authority pertaining to International Application No. PCT/US2020/013985; International filing date: Jan. 17, 2020; dated Apr. 28, 2020.
(Continued)

*Primary Examiner* — Kendra D Carter
*Assistant Examiner* — Elliot S Ruddie
(74) *Attorney, Agent, or Firm* — M. Daniel Spillman

(57) ABSTRACT

Embodiments described herein describe a drug delivery device. The device includes a medicament container, a compressed gas container, an outlet, and a double-sided needle located within the housing. When a user presses an actuation button, the compressed air container is moved towards the medicament container and towards a proximal end of the double-sided needle. The double-sided needle
(Continued)

pierces both the compressed gas container and the medicament container, opening fluid flow communication between the two containers, and causing medicament to be expelled out of the medicament container.

15 Claims, 10 Drawing Sheets

(52) U.S. Cl.
CPC ... *A61M 15/0041* (2014.02); *A61M 2202/064* (2013.01); *A61M 2205/8218* (2013.01); *A61M 2205/8281* (2013.01); *A61M 2210/0618* (2013.01)

(58) Field of Classification Search
CPC .............. A61M 5/2046; A61M 5/2466; A61M 5/2474; A61M 5/30; A61M 11/02; A61M 15/08; A61M 15/0035–0041; A61M 15/0001; A61M 16/14; A61M 2005/247; A61M 2202/02; A61M 2202/064; A61M 2205/8218–8225; A61M 2205/8275–8281; A61M 2210/0618
USPC .................. 128/203.15; 604/82–86
See application file for complete search history.

(56) References Cited

U.S. PATENT DOCUMENTS

| | | |
|---|---|---|
| 6,406,455 B1 | 6/2002 | Willis et al. |
| 6,960,184 B2 | 11/2005 | Willis et al. |
| 9,033,939 B2 | 5/2015 | Eberhart et al. |
| 2014/0053835 A1* | 2/2014 | Gilbert .................. A61M 15/08 |
| | | 128/203.14 |
| 2019/0015613 A1* | 1/2019 | Shahaf .................. B05B 11/061 |

FOREIGN PATENT DOCUMENTS

| | | |
|---|---|---|
| JP | 2001095918 | 4/2001 |
| WO | 2016142527 | 9/2016 |

OTHER PUBLICATIONS

Patent Cooperation Treaty Written Opinion of the International Searching Authority pertaining to International Application No. PCT/US2020/013985; International filing date: Jan. 17, 2020; dated Apr. 28, 2020.

* cited by examiner

NASAL DRUG DELIVERY DEVICES

FIELD

Embodiments disclosed herein relate to devices and methods for delivering drugs.

BACKGROUND

Some medications or other substances may be administered to the human body through nasal administration or inhalation. These drugs and substances can be stored as a powder or liquid and are aerosolized or otherwise propelled into the nose or mouth of a patient. Some medications may be self-administered by a patient. Some medication dispensers may be portable to allow patients to access their medications while away from home and/or a healthcare facility.

SUMMARY

According to one embodiment, a nasal drug delivery device comprises a housing, an outlet, an actuation button, a medicament container containing a powdered medicament, a compressed gas container containing a sterile compressed gas (such as air, or some other suitable gas), and a first needle configured to pierce the medicament container in response to actuation of the actuation button. Fluid flow communication between the medicament container and the compressed gas container is closed prior to actuation of the actuation button. Actuation of the actuation button opens fluid flow communication between the medicament container and the compressed gas container to expel the powdered medicament from the medicament container out of the outlet.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Provided herein is a drug delivery device that is configured to expel a medicament using a predetermined amount of potential energy, e.g., using energy stored within the device. In some embodiments, the drug delivery device includes stored compressed gas as its stored energy source. According to one aspect, the force at which medicament is expelled from the drug delivery device is consistent with each actuation instead of varying based on the amount of force exerted upon the device by a user resulting in a consistent predetermined drug dispersion plume.

According to another aspect, the drug delivery device may include an actuation arrangement in which fluid flow communication between a compressed gas container and a medicament container is opened in response to actuation of the device. In some embodiments, the containers are pierced in response to actuation of the device to open fluid flow communication between the containers. In some embodiments, the medicament container is pierced prior to the compressed gas container being pierced. A double-sided needle may, in some embodiments, be used to pierce the containers. The needle may be hollow or solid. In some embodiments, the needle is part of a needle hub that is moveable within the drug delivery device, and may be moveable relative to the medicament container and/or relative to the compressed gas container. The compressed gas container may be moveable relative to the housing of the drug delivery device and/or to the medicament container. The actuation arrangement may, in some embodiments, include biasing members such as springs. The biasing members may facilitate sequential piercing of the containers.

In some embodiments, the drug delivery device may be a nasal drug delivery device that delivers a powdered medicament. The term "medicament" refers to one or more therapeutic agents including but not limited to glucagon, glucagon analogs, and glucagon derivatives. The term "medicament" may also include (but is not limited to) any therapeutic agent that may be stored in powdered form and that is capable of delivery by the disclosed drug delivery device.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

Figure 1:
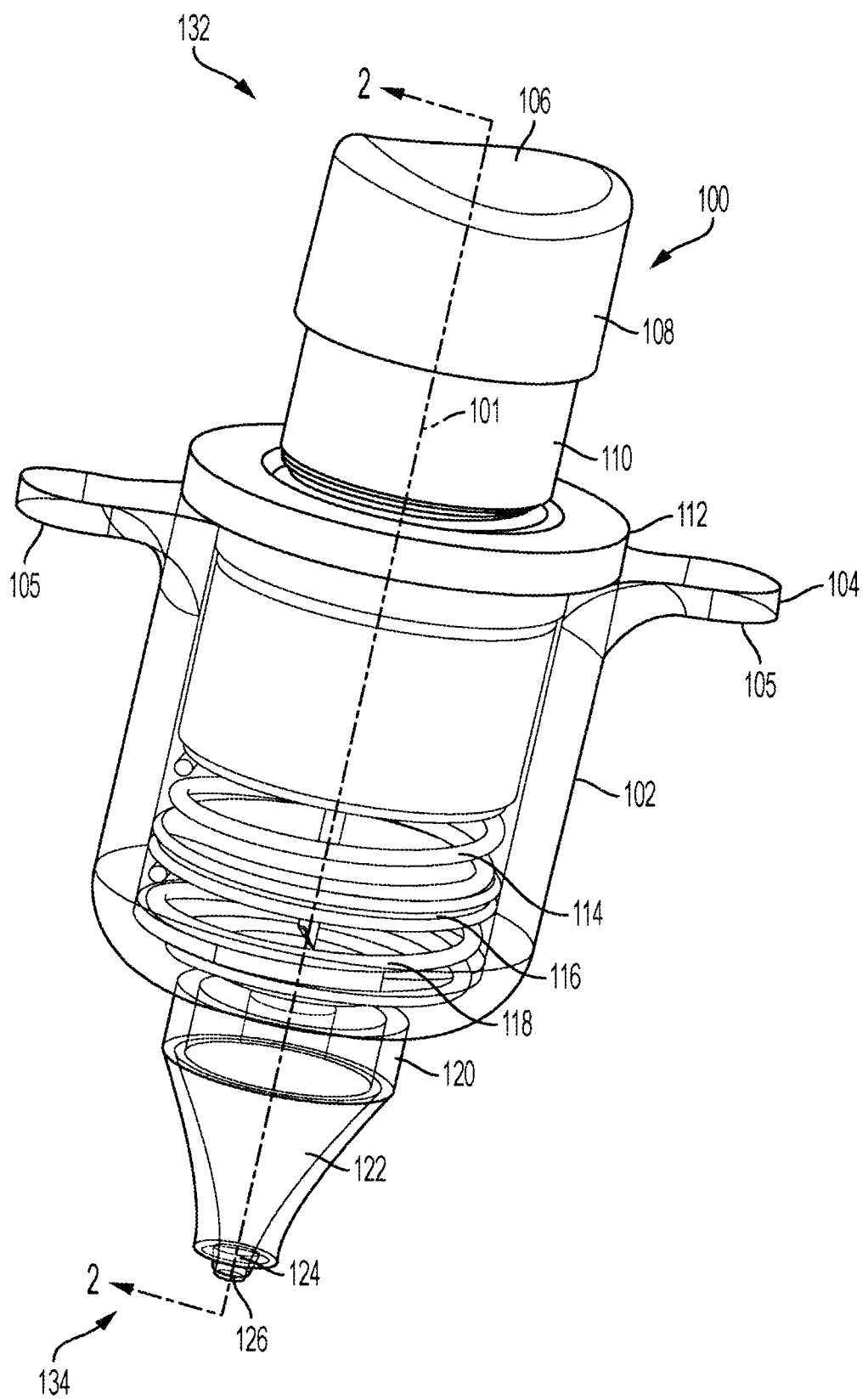
FIG. 1 is a perspective view of a drug delivery device according to one embodiment, with a housing shown in phantom.

FIG. 1 shows a perspective view of a drug delivery device 100 having a proximal end 132 and a distal end 134. The drug delivery device includes a housing 102 with grips 104 extending laterally from the housing. Housing 102 at least partially contains a compressed gas container 110 at the proximal end 132 of the device. Cap 108 covers the proximal end of the compressed gas container 110 and provides a pressing surface for button 106. Housing end 112 helps physically retain compressed gas container 110 within the housing 102 while allowing the compressed gas container to translate within a limited range along a longitudinal axis 101 of the drug delivery device 100. Housing end 112 also serves as a sterile barrier for the needle assembly by preventing non-sterile atmosphere from reaching the interior of housing 102. The distal end 134 of the housing transitions into bottleneck 120, and ends in medicament container 122. Medicament may be expelled out of the medicament container 122 from an outlet 126 in nozzle 124. Outlet 126 may have a frangible membrane, stiff baffles, removable seal, or other suitable cover that prevents the powdered medicament from leaking out prior to delivery.

In the illustrative embodiment of FIG. 1, medicament container 122 is contained within nozzle 124. It should be understood, however, that the medicament container 122 can be of any shape and may, in some embodiments, extend into the rest of housing 102.

Figure 2:
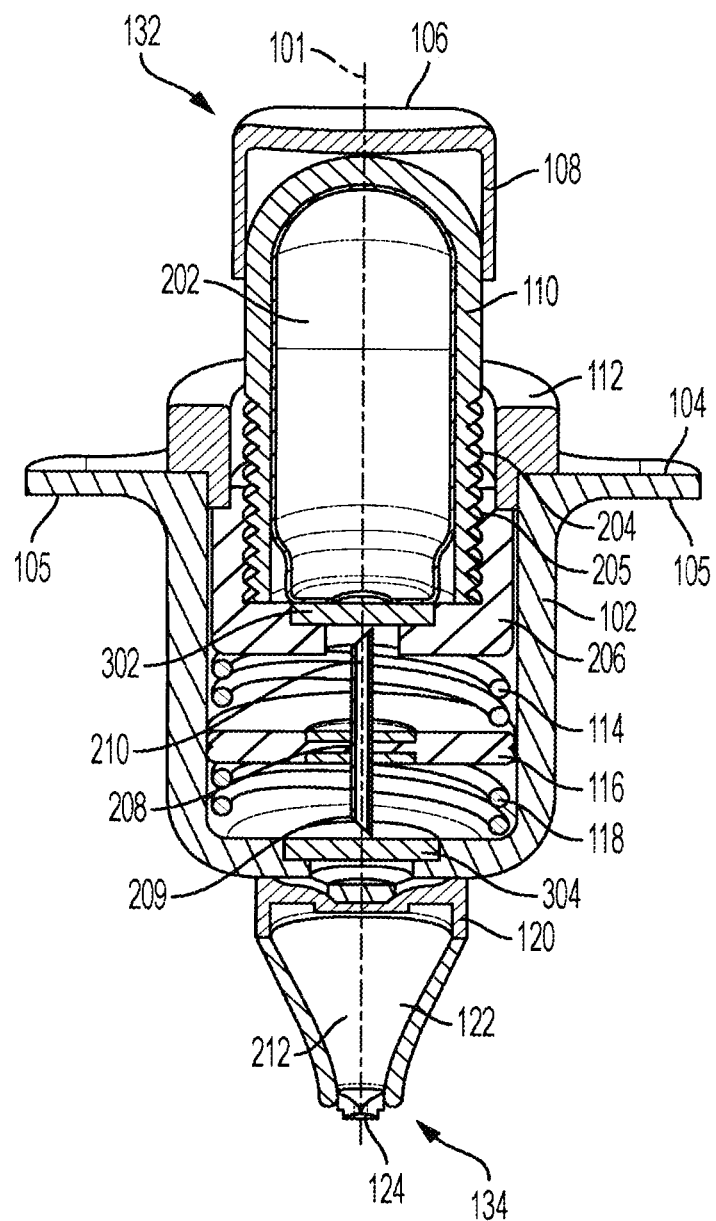
FIG. 2 is a front, cross-sectional view of the drug delivery device of FIG. 1, taken along line 2-2 of FIG. 1.

FIG. 2 shows a cross-sectional view of the drug delivery device 100 taken along line 2-2 of FIG. 1. Compressed gas is contained within compressed gas container interior 202, and is held within, and sealed, by proximal septum 302. A powdered medicament may be contained in medicament container interior 212, and prevented from entering the rest of housing 102, and sealed by distal septum 304.

Drug delivery device 100 further includes a needle hub 116 comprising a moveable disk that is coupled to a double-sided needle 208. A moveable shelf 206 within housing 102 is coupled to the compressed gas container 110, and serves to allow the compressed gas container to move relative to the housing and the medicament container.

In some embodiments, an outer surface of the compressed gas container may be threaded and may be configured to interact with corresponding threads in an interior surface of the moveable shelf 206 to attach the compressed gas container to the moveable shelf. Compressed gas container threads 204 and moveable shelf threads 205 are shown in FIG. 2. It should be understood that other methods of attachment are contemplated including a pressure fit, friction fit, or other method of retaining the compressed gas container.

In some embodiments, the drug delivery device may include biasing members to aid in delivery of the medicament. Proximal biasing member 114 is located proximal to the needle hub 116 and distal to the moveable shelf 206. Distal biasing member 118 is located distal to the needle hub and proximal to bottleneck 120 and medicament container 122. While the proximal and distal biasing members are depicted as compression coil springs in this embodiment, it should be understood that any biasing or elastic force generating arrangement is also contemplated. Other embodiments of biasing members include, but are not limited to Belleville springs (also called Belleville washers), leaf springs, or solid blocks of material with potential energy storing properties such as elastomers, foam, or rubber.

Double-sided needle 208 is comprised of proximal needle 210 and distal needle 209. The distal needle serves as a first end of the double-sided needle 208, and the proximal needle serves as a second end of double-sided needle 208. The proximal needle 210 is configured to pierce the proximal septum 302 of the compressed gas container 110, and the distal needle 209 is configured to pierce the distal septum 304 of the medicament container 122. In some embodiments, the double-sided needle may be hollow to allow fluid flow communication between both ends of the double-needle.

In other embodiments, however, the double-sided needle is solid. With a solid needle, fluid flow communication between the compressed gas container and the medicament container may still be possible, e.g. after the compressed air container septum is pierced, compressed air may escape from the compressed air container and enter the medicament container. The needles may form imperfect seals against the septa they pierced, allowing compressed air to travel through the pierced septa around the needle. Alternatively, the needles may be retracted away from the compressed air container septum and/or the medicament container septum to open fluid flow communication between the two containers.

In some embodiments, instead of a single needle having two piercing ends, the drug delivery device may include two separate and distinct needles, each having a single piercing end.

It should be understood that the housing can be of any length and shape as needed to contain the needle, compressed gas container, and medicament container. The compressed gas container can be of any size or shape needed to contain the volume and pressure of the gas needed for the type of medicament to be delivered. Similarly, the medicament container can be of any shape and size as needed to contain the medicament to be delivered.

To operate the drug delivery device, a user begins by aiming the nozzle 124 into their nostril, and then pressing button 106, thereby actuating the button and compressed gas container 110 to move distally relative to the medicament container 122. The user may grip grips 104 to assist with leverage when pressing button 106. For example, the user may place their thumb on the button 106 and hook their index and middle fingers around the distal surfaces 105 of the grips 104, and then press their thumb toward their index and middle fingers to press button 106.

In some embodiments, the proximal and distal biasing members of the drug delivery device are designed to have different stiffnesses/spring constants such that the proximal biasing member 114 is stiffer or otherwise harder to deform or compress than the distal biasing member 118.

As the compressed gas container moves, proximal septum 302 and moveable shelf 206 approach proximal needle 210, causing moveable shelf 206 to exert a force on the proximal biasing member 114 in the process. In some embodiments, the distal biasing member 118 has lower stiffness than the proximal biasing member 114. Thus, the distal biasing member 118 compresses first, prior to compression of the proximal biasing member 114. The initial exertion of force on the proximal biasing member 114 from the moveable shelf 206 causes the needle hub 116 to move distally and the distal biasing member 118 to compress rather than causing the proximal biasing member 114 to compress. There may be some slight compression of proximal biasing member 114, but it is the distal biasing member 118 that reaches full compression first. As needle hub 116 moves distally during compression of the distal biasing member 118, distal needle 209 moves distally towards distal septum 304.

Figure 3:
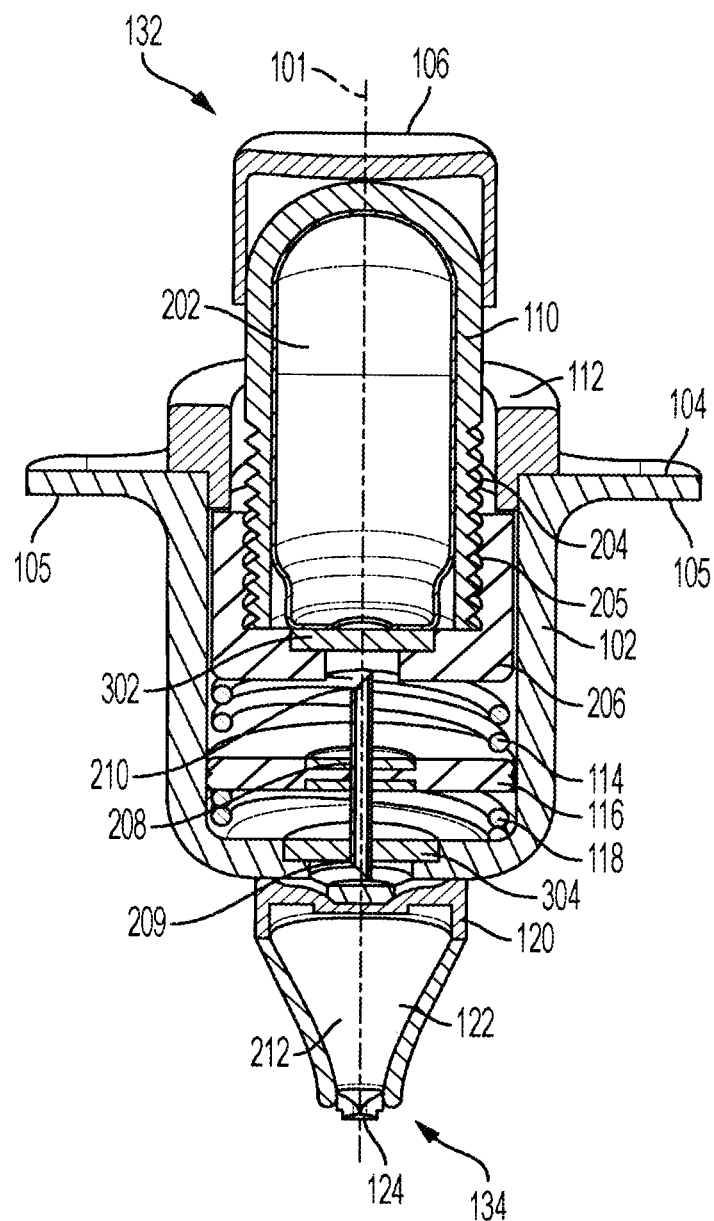
FIG. 3 is a front, cross-sectional view of the drug delivery device of FIG. 1, taken along line 2-2 of FIG. 1, after usage of the device has begun, but before the medicament is discharged.

FIG. 3 shows the drug delivery device 100 after the actuation of button 106, but before fluid flow communication has been opened between the medicament container and the compressed gas container. At this intermediate stage, as seen in the figure, distal needle 209 has pierced distal septum 304, but proximal needle 210 has yet to pierce proximal septum 302 despite distal movement of the compressed gas container 110. The proximal biasing member 114 has a stiffness such that the force required for the distal needle to pierce the distal septum is less than the force required to compress the proximal biasing member the distance needed for the proximal needle to start piercing the proximal septum. Alternatively or in addition, the proximal septum and/or proximal needle are tuned to require a greater force for the proximal needle to pierce the proximal septum than the distal needle to pierce the distal septum. As a result, the medicament container septum is pierced before the gas container septum is pierced.

Figure 4:
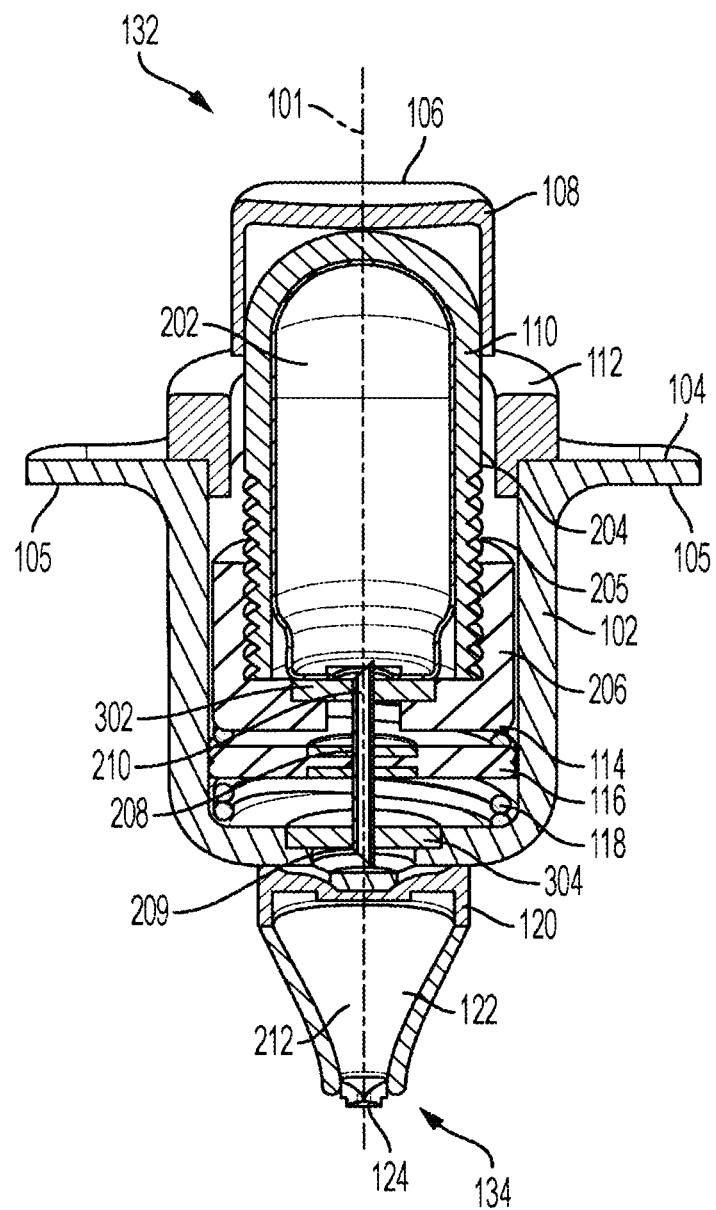
FIG. 4 is a front, cross-sectional view of the drug delivery device of FIG. 1, taken along line 2-2 of FIG. 1, during medicament delivery.

After the medicament container septum is pierced, continued exertion of force onto button 106 and compressed gas container 110 from the user fully or partially compresses proximal biasing member 114 because needle hub 116 cannot be moved further distally due to distal biasing member 118 being at maximum or close to maximum compression. As such, the proximal biasing member compresses, allowing proximal septum 302 to be punctured by proximal needle 210 as seen in FIG. 4.

Fluid flow communication is established between the compressed gas container and the medicament container when the needle has pierced through both the distal septum 304 and the proximal septum 302. With the needle 208 being hollow, powdered medicament in medicament container 122 is first fluidly connected to the double-sided needle 208, followed shortly thereafter by compressed gas from compressed gas container 110 being placed in fluid flow communication with the medicament container 122 via the double-sided needle 208. Piercing the medicament container prior to the compressed gas container may prevent potential loss of medicament from early exposure to compressed gas, and/or may prevent pressure from building up in the housing and/or needle. As soon as fluid flow communication is established, compressed gas escapes compressed gas container 110 distally through and/or around double-sided needle 208. The rapid gas movement causes the powdered medicament to be expelled from outlet 126 of nozzle 124 at an appropriate pressure and dispersion level to deliver the powdered medicament.

It is contemplated that the described arrangement of having to compress the proximal and distal biasing members to trigger dispensing of the medicament can have a variety of advantages. For instance, having the biasing members define the maximum possible distal movement of the compressed gas container may enable greater tolerances when manufacturing the housing and compressed gas container.

Some embodiments of the drug delivery system may be designed to yield an audible click when the button and compressed gas container is depressed to an appropriate level. For example, cap 108 may be designed with features that interact with corresponding features on compressed gas container 110, and which flex or move slightly as cap 108 is depressed, thus giving rise to an audible click. In some embodiments, once cap 108 has been depressed sufficiently, it may lock into place into housing end 112, thus preventing cap 108 from popping back out again. This would also indicate to a user that the device has been actuated.

Figure 5:
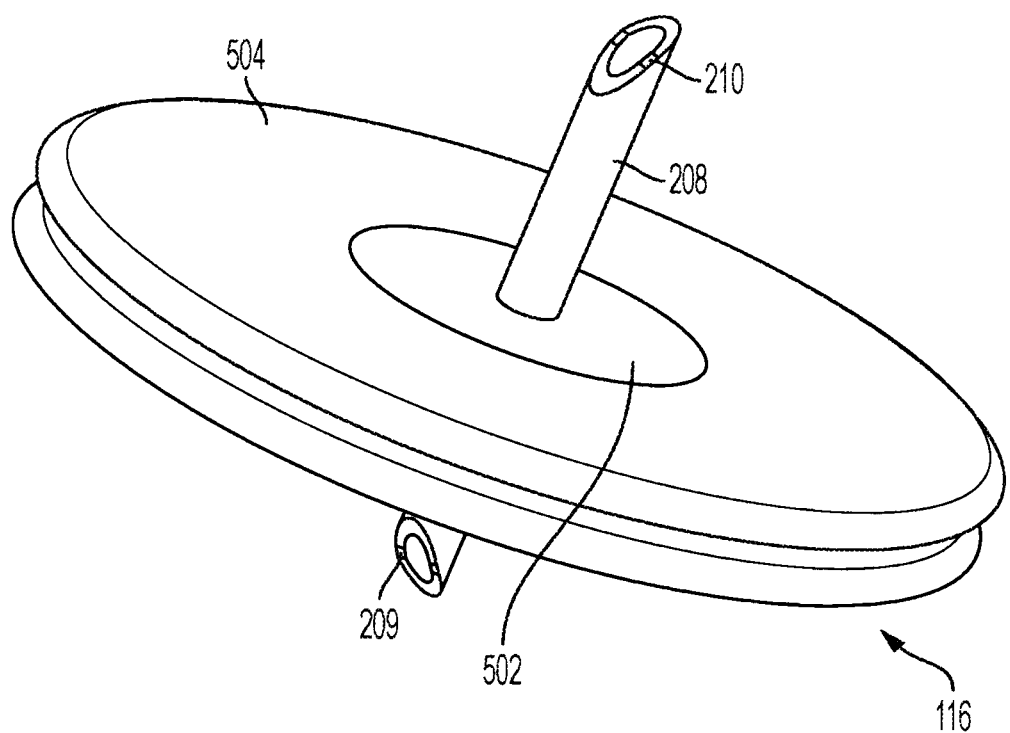
FIG. 5 is a perspective view of a needle hub and double-sided needle of the drug delivery device according to one embodiment.
Figure 6:
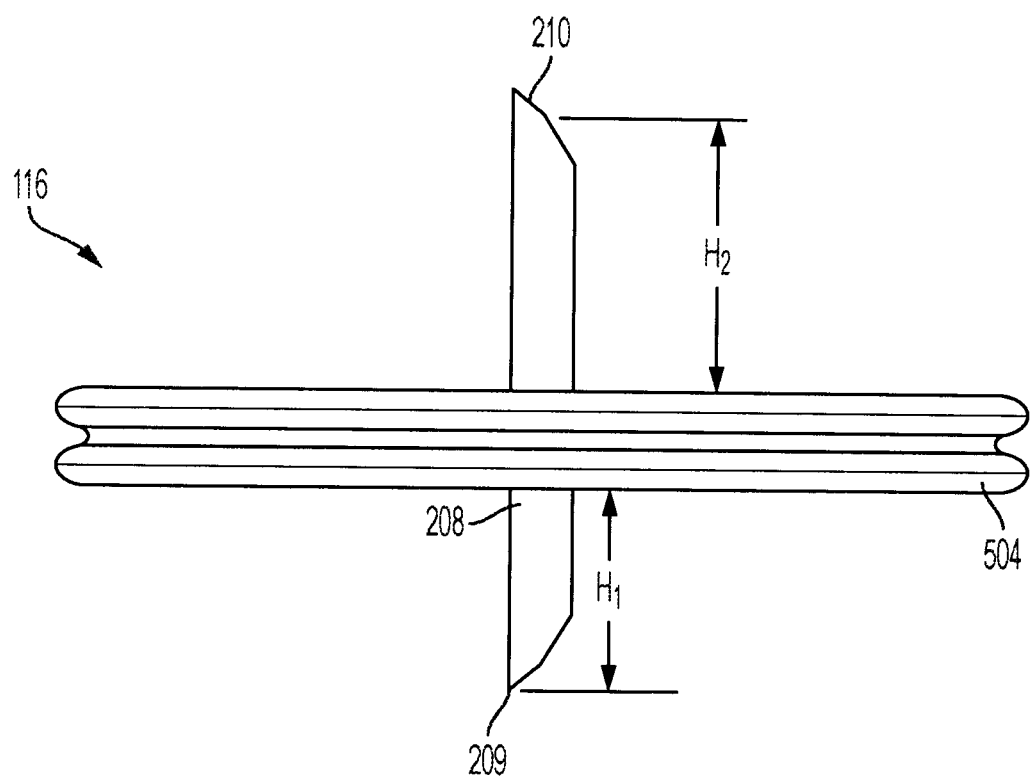
FIG. 6 is a side view of the needle hub and double-sided needle of FIG. 5.

FIG. 5 shows the needle hub according to one embodiment of the drug delivery device, and FIG. 6 shows a front view of the needle hub. Double-sided needle 208 passes through needle hub 116. Retaining portion 502 may be comprised of stiff retaining plates that are glued or otherwise attached to the needle 208 and a disk 504 to stabilize the needle. The disk may be made of a material that is less stiff than the retaining portion. For example, the disk may be made of an elastomeric material. Disk 504 may be sized such that the proximal biasing member 114 can push against needle hub 116, which may in turn push against and compress distal biasing member 118. The disk may be sized to be the same size, slightly larger or slightly smaller than an inner diameter of the housing to avoid excessive tilting of the needle hub during movement of the needle hub, thus promoting piercing of the septa of the containers. Where the elastomeric disk is the same size or slightly larger than the inner diameter of the housing, the material of the disk may promote sliding engagement between the outer perimeter of the disk and the inner walls of the housing. The device may include other features such as bearings and/or lubricant to promote sliding of the disk against the inner walls of the housing.

As seen in FIG. 6, the height ($H_1$) of distal needle 209 is less than the height ($H_2$) of proximal needle 210 in this embodiment. In some embodiments, $H_1$ may be between 2 to 5 mm, between 3 to 4 mm, or between 3.5 to 3.8 mm. In some embodiments, $H_2$ may be between 3 to 7 mm, between 4 to 6 mm, between 4.5 to 5.5 mm, or between 4.9 to 5.1 mm.

Figure 7:
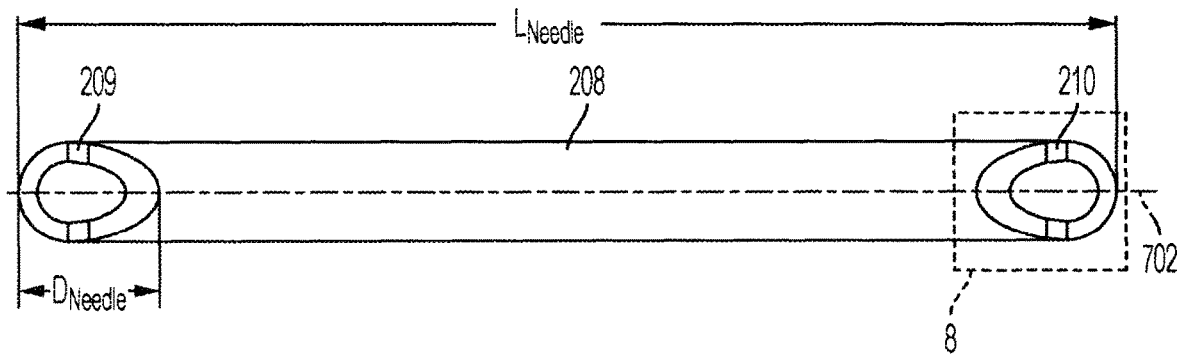
FIG. 7 is a front view of the double-sided needle of a drug delivery device according to one embodiment.
Figure 8:
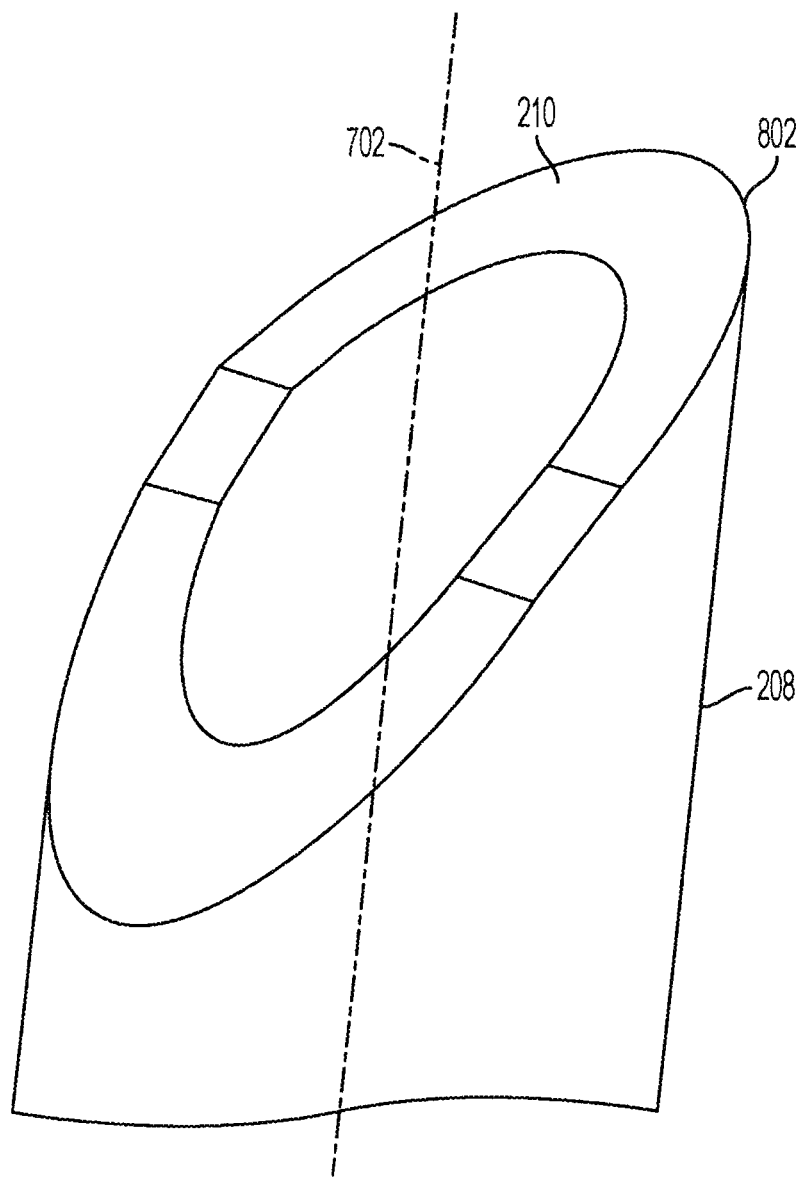
FIG. 8 is a close-up view of region 8 of FIG. 7.

FIG. 7 shows the double-sided needle 208 in isolation. The ends of double-sided needle may be beveled to create a leading edge 802 to pierce the septa, as seen in FIG. 8, which shows a close-up of region 8 of FIG. 7. Line 702 denotes the longitudinal axis of the double-sided needle 208, which may be coincident with the longitudinal axis 101 of the drug delivery device. The needle may be a 10 gauge needle, a 9 gauge needle, an 8 gauge, needle, or other suitable sized needle. As shown in FIG. 7, the needle may have a total length $L_{Needle}$ of between 8 to 14 mm, between 9 to 13 mm, between 10 to 12 mm, or between 11-11.5 mm. The beveled ends of the needle may have a length $D_{Needle}$ of about 0.5 mm to 2 mm, or about 1 to 1.8 mm, or about 1.3 to about 1.4 mm.

It is contemplated that having a proximal needle that is longer than the distal needle may be beneficial to ensure full puncture of the proximal septum, which may be thicker than the distal septum in some embodiments to properly contain the pressurized compressed gas and/or to promote piercing of the medicament container septum prior to piercing of the compressed gas container. However, other embodiments are contemplated where the proximal needle may be the same height or shorter than the distal needle. In these embodiments, the relative heights or stiffnesses of the proximal and distal biasing members may be adjusted such that the proximal septum is fully punctured when the button is pressed, but is only punctured after the distal septum has been punctured by the distal needle.

By having both the medicament container and the compressed gas container separately sealed, in some cases, it could take more than one septa to fail to potentially compromise the device.

Having a double-sided needle initially spaced from the container septa prior to device actuation may have some benefits. By requiring that the septa be brought to the needles or vice versa rather than having the septa already partially pierced prior to actuation, the undamaged septa may have a longer lifespan, and more durability when the device is being moved around. Avoiding the need to have the needles already partially pierce the septa prior to device actuation may allow for greater tolerance in needle length and positioning when manufacturing the device. Further, piercing the septa only in response to actuation of the device button may help to maintain sterility and stability of the medicament.

Figure 9:
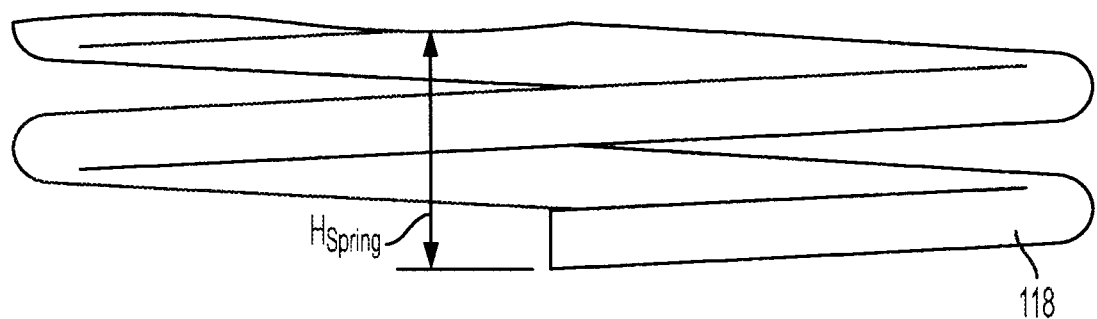
FIG. 9 is a partial front view of a distal biasing member of the drug delivery device according to one embodiment.
Figure 10:
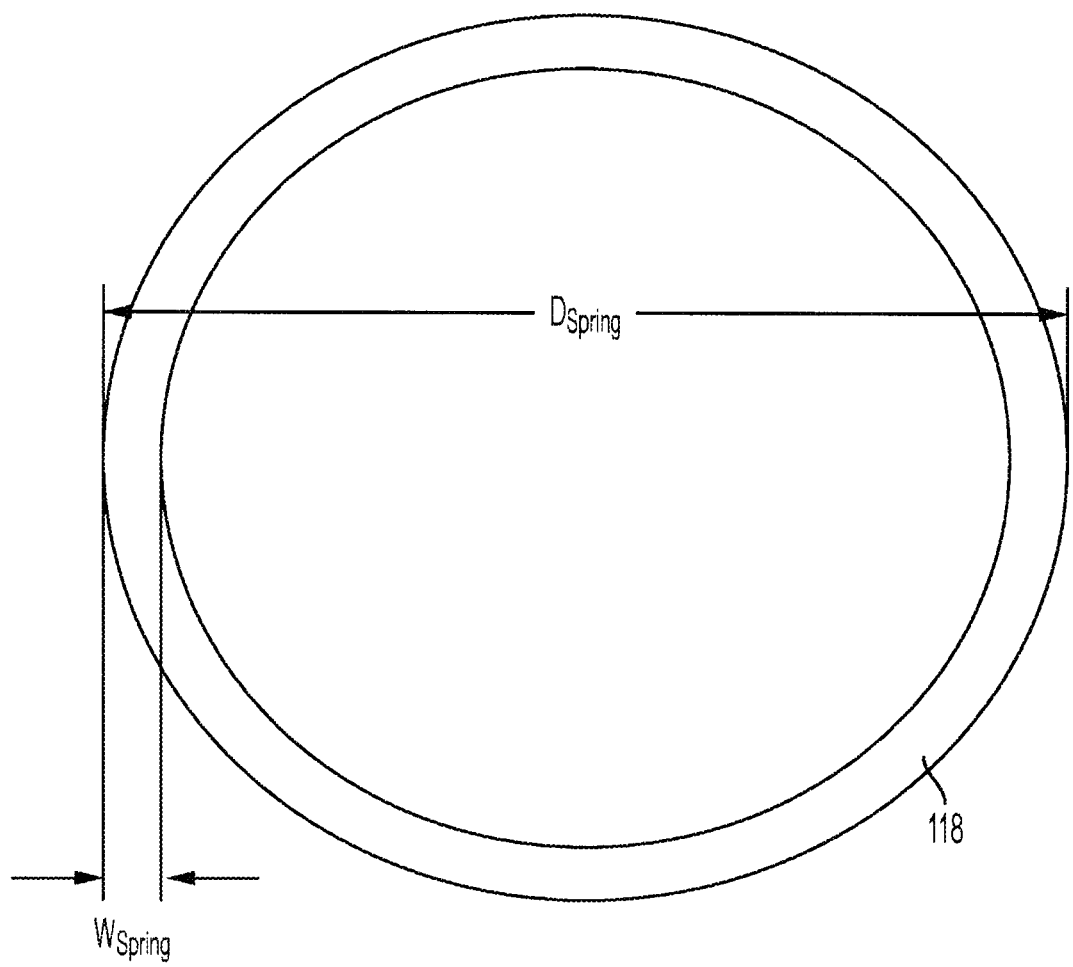
FIG. 10 is a top view of the distal biasing member of FIG. 9.

FIG. 9 shows a side view of the distal biasing member 118 embodied as a spring, and FIG. 10 shows a top view of the distal biasing member. The distal biasing member has a height ($H_{spring}$), thickness ($W_{spring}$) and diameter ($D_{spring}$).

The height, thickness, diameter, material, and coil density of the spring can all be adjusted to adjust the stiffness of the spring to adjust how much force is necessary to compress the spring. Proximal biasing member may also be embodied as a spring, and may look similar of identical to the distal biasing member, but made of a different material to give it additional stiffness. Proximal biasing member may also have a greater $H_{spring}$, or a thicker thickness, or both, or neither as well.

In some embodiments, the height $H_{spring}$ of the distal biasing member is between 2 to 5 mm, or between 3 to 4.5 mm, or between 3.5 to 4.2 mm, or between 3.7 to 3.9 mm. In some embodiments, the thickness $W_{spring}$ of the biasing member is between 0.5 to 1.5 mm, or between 0.8 to 1.2 mm, or between 0.9 to 1.1 mm, or 1 mm. In some embodiments, the diameter $D_{spring}$ of the biasing member is between 10 to 20 mm, or between 12 to 18 mm, or between 14 to 17 mm, or between 15 to 16 mm, or between 15.6 to 15.8 mm.

While the above embodiments have been described in relation to a drug delivery device for delivering a powdered medicament, it should be understood that liquid medicaments can also be utilized. Embodiments with a liquid medicament may include additional specialized tubing or structures to assist in aerosolization of the liquid medicament located in the nozzle or at the outlet.

The above teachings may also be applied to dispensation of medicaments in non-nasal administrations. For instance, the nozzle may be directed into a user's mouth, or over a wound, or some other site for administration. These embodiments may have nozzles shaped to facilitate the desired dispensation distribution depending on the application.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the embodiments described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "user." It should be appreciated that a "user" need not be a single individual, and that in some embodiments, actions attributable to a "user" may be performed by a team of individuals and/or an individual in combination with computer-assisted tools or other mechanisms. Use of the device is not limited to self-administration. A "user" can be someone who uses the device to administer the medicament to another person.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

What is claimed is:

1. A nasal drug delivery device, comprising:
   a housing;
   an outlet;
   an actuation button;
   a medicament container containing a powdered medicament;
   a compressed gas container containing a compressed gas, fluid flow communication between the medicament container and the compressed gas container being closed prior to actuation of the actuation button;
   a first needle configured to pierce the medicament container in response to actuation of the actuation button; and
   a second needle configured to pierce the compressed gas container in response to actuation of the actuation button,
   wherein the actuation button is configured to be actuated to open fluid flow communication between the medicament container and the compressed gas container to expel the powdered medicament from the medicament container out of the outlet.

2. The nasal drug delivery device of claim 1, wherein the first needle and the second needle form a double-sided needle, wherein the first needle is at a first end of the double-sided needle and the second needle is at a second end of the double-sided needle.

3. The nasal drug delivery device of claim 2, wherein the double-sided needle is hollow such that the medicament container fluidly communicates with the compressed gas container through the double-sided needle after the double-sided needle has pierced the medicament container and the compressed gas container.

4. The nasal drug delivery device of claim 1, wherein the first needle is configured to pierce the medicament container before the second needle pierces the compressed gas container.

5. The nasal drug delivery device of claim 4, further comprising a needle hub attached to the first needle and the second needle, the needle hub being moveable relative to the housing and being positioned between the medicament container and the compressed gas container.

6. The nasal drug delivery device of claim 5, wherein the first needle and the second needle form a double-sided needle, wherein the first needle is at a first end of the double-sided needle and the second needle is at a second end of the double-sided needle, and the double-sided needle passes through the needle hub.

7. The nasal drug delivery device of claim 5, further comprising a first biasing member positioned between the medicament container and the needle hub, and a second biasing member positioned between the compressed gas container and the needle hub.

8. The nasal drug delivery device of claim 7, wherein the first biasing member comprises a first spring and the second biasing member comprises a second spring.

9. The nasal drug delivery device of claim 8, wherein a stiffness of the first spring is different from a stiffness of the second spring.

10. The nasal drug delivery device of claim 9, wherein the stiffness of the first spring is less than the stiffness of the second spring.

11. The nasal drug delivery device of claim 1, wherein the compressed gas container is moveable relative to the medicament container and moves relative to the medicament container in response to actuation of the actuation button.

12. The nasal drug delivery device of claim 11, wherein the actuation button is attached to the compressed gas container such that actuation of the actuation button moves the compressed gas container toward the medicament container.

13. The nasal drug delivery device of claim 1, further comprising a distal septum sealing the medicament container closed, wherein the first needle is configured to pierce the distal septum.

14. The nasal drug delivery device of claim 1, further comprising a proximal septum sealing the compressed gas container closed, wherein the second needle is configured to pierce the proximal septum.

15. The nasal drug delivery device of claim 1, wherein the powdered medicament comprises glucagon.

* * * * *